(12) United States Patent
Wofford et al.

(10) Patent No.: US 6,322,249 B1
(45) Date of Patent: Nov. 27, 2001

(54) SYSTEM AND METHOD FOR AUTOMATIC CALIBRATION OF A MULTILEAF COLLIMATOR

(75) Inventors: Mark Wofford, Martinez; Francisco M. Hernandez-Guerra, Concord, both of CA (US)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 0 days.

(21) Appl. No.: 09/493,693

(22) Filed: Jan. 28, 2000

Related U.S. Application Data

(63) Continuation-in-part of application No. 09/360,927, filed on Jul. 26, 1999, now Pat. No. 6,260,999.

(51) Int. Cl.[7] .................................................. G01D 18/00
(52) U.S. Cl. .......................... 378/207; 378/205; 378/204; 378/65; 378/152
(58) Field of Search ..................................... 378/152, 162, 378/163, 206, 204, 205, 207, 64, 65

(56) References Cited

U.S. PATENT DOCUMENTS

| | | | |
|---|---|---|---|
| 4,882,741 | * 11/1989 | Brown | 378/152 |
| 5,166,531 | * 11/1992 | Huntzinger | 250/505.1 |
| 5,654,996 | * 8/1997 | Steinberg et al. | 378/65 |
| 6,056,437 | * 5/2000 | Toth | 378/205 |
| 6,141,402 | * 10/2000 | Toth | 378/150 |
| 6,260,999 | * 7/2001 | Wofford et al. | 378/205 |

\* cited by examiner

*Primary Examiner*—David V. Bruce
*Assistant Examiner*—Allen C. Ho

(57) ABSTRACT

The present invention relates to a system and method for calibrating a radiation therapy device, such as a collimator. A method for calibrating a collimator according to an embodiment of the present invention is presented. The method comprises moving a leaf of a collimator; determining whether a distance between the leaf and a line approximately equals a predetermined measurement; and associating the predetermined measurement with a collimator specific count if the distance between the leaf and the line approximately equals the predetermined measurement.

13 Claims, 10 Drawing Sheets

SYSTEM AND METHOD FOR AUTOMATIC CALIBRATION OF A MULTILEAF COLLIMATOR

CROSS REFERENCE TO RELATED APPLICATION

This application is a continuation-in-part of U.S. application Ser. No. 09/360,927, entitled "Isocenter Localization Using Electronic Portal Imaging," filed Jul. 26, 1999, now U.S. Pat. No. 6,260,999 which is herein incorporated by reference for all purposes.

FIELD OF THE INVENTION

The present invention relates to imaging systems, typically used for radiation treatment. In particular, the present invention relates to imaging systems for linear accelerators (linacs) which may be used in radiation therapy.

BACKGROUND OF THE INVENTION

The use of a linear accelerator in radiation therapy is generally known. Such linear accelerators are typically used for treating patients with x-rays or electron beams. Such x-rays are created when high energy electrons are decelerated in a target material such as tungsten. Alternatively, the electrons themselves may be used directly for treatment.

The major modules in a linear accelerator typically include a movable gantry with a treatment head, a stand, a control console and a treatment couch. The stand is typically anchored firmly to the floor and the gantry typically rotates on bearings in the stand. The operational accelerator structure, housed in the gantry, typically rotates about a horizontal axis fixed by the stand for treatment of a patient lying on the treatment couch.

In the radiation therapy treatment of a patient, geometric accuracy is a very important factor to the success of the treatment. The goal is commonly to hit a specific target, such as a tumor, and miss critical regions of the patient's body, such as the spine. Properly positioning the patient may be a critical issue in avoiding damage to tissue and critical organs. Typically, within reason, the more accurate the x-ray delivery to the exact target, the higher the dose a patient may receive.

An electronic portal image may be captured for the purpose of determining whether the target on the patient is within the treatment beam and whether critical regions of the patient are missed. Typically, people are responsible for taking these images and determining if the patient is positioned correctly. If film is used for the image, then the film must typically be developed and placed next to a reference image to compare the two images. The reference image is typically an x-ray image, which has been marked up by the patient's doctor. The two images are typically compared to ensure that the area which is actually being treated is the same area that the patient's doctor has marked up in the reference image. This comparison is typically a visual comparison. A technician may visually compare the two images and try to match visual landmarks between the two images. A potential problem with this visual comparison is human error in the comparison between the two images. The person making the comparison is commonly looking for very small errors, on the order of millimeters, which are normally very difficult to visually compare.

Another issue which may compound the problem is that high energy x-ray is commonly used. Accordingly, most of the x-ray goes through the body of the patient and a bony landmark is typically needed to give the person making the comparison an indication of the image reference. This visual comparison between a vague patient positioning image and a reference image may be substantially inaccurate.

Electronic portal imaging systems may produce an image without the use of film, however, a person still needs to visually compare the resulting image with a reference image. Some measuring tools may be used on the electronic portal imaging, however, the comparison is still substantially a manual process.

Although there are known algorithms for comparing two images electronically, there is typically no way of ensuring that the two images may be compared with the same frame of reference to ensure a proper match. The frame of reference of the portal imaging device is typically unknown due to mechanical errors. The gantry of the portal imaging device typically rotates around the patient. When the gantry is rotated, there is commonly a mechanical sag of the detector assembly in the imaging system which may shift the frame of reference of the image. Additionally, the detector housing of the imaging device is typically retractable into the gantry and the detector housing may not be exactly in the same position every time it is extended. Although the mechanical sag may be fairly slight, a millimeter or half a millimeter may still make a difference in patient positioning. Accordingly, the image may be offset compared to the reference image.

Once an image has been compared to the reference image, a multi-leaf collimator may be used to direct the treatment beam onto a selected area of the patient. However, without a well defined point of reference, the collimator may direct the treatment beam slightly off target.

Manual calibration typically requires large and unwieldy components, such as a large water tank, and a trained operator to mount and put together the various components in preparation for calibration. Calibration typically requires three to four hours. Accordingly, calibration is typically performed only about once a month with a check approximately once a week to insure that the collimator is still properly calibrated. If the check shows that the collimator is not properly calibrated, then it is typically determined whether the collimator is within an acceptable margin of error. There may be a reluctance to frequently calibrate the collimator due to the large amount of required work and time and the disruption in the scheduling of the treatments.

What is needed is a system and method for calibration that is fast and simple, without the need for additional equipment. The present invention addresses such a need.

For further background information on the construction and operation of a typical radiation therapy device, a brochure entitled "A Primer On Theory And Operation Of Linear Accelerators In Radiation Therapy", U.S. Department of Commerce, National Technical Information Service, December 1981, may be referenced.

SUMMARY OF THE INVENTION

The present invention relates to a system and method for calibrating a radiation therapy device, such as a collimator. A method for calibrating a collimator according to an embodiment of the present invention is presented. The method comprises moving a leaf of a collimator; determining whether a distance between the leaf and a line approximately equals a predetermined measurement; and associating the predetermined measurement with a collimator specific count if the distance between the leaf and the line approximately equals the predetermined measurement.

A system for calibrating a collimator according to an embodiment of the present invention is also presented. The system comprises means for moving a leaf of a collimator; means for determining whether a distance between the leaf and a line approximately equals a predetermined measurement; and means for associating the predetermined measurement with a collimator specific count if the distance between the leaf and the line approximately equals the predetermined measurement.

Another system for calibrating a collimator according to an embodiment of the present invention is also presented. The system comprises a collimator including a leaf; an image capturing device configured to capture an image of the collimator; and a processor configured to determine whether a distance between the leaf and a line approximately equals a predetermined measurement.

DETAILED DESCRIPTION OF THE PREFERRED EMBODIMENTS

The following description is presented to enable one of ordinary skill in the art to make and to use the invention and is provided in the context of a patent application and its requirements. Various modifications to the preferred embodiments will be readily apparent to those skilled in the art and the generic principles herein may be applied to other embodiments. Thus, the present invention is not intended to be limited to the embodiments shown but is to be accorded the widest scope consistent with the principles and features described herein.

Figure 1:
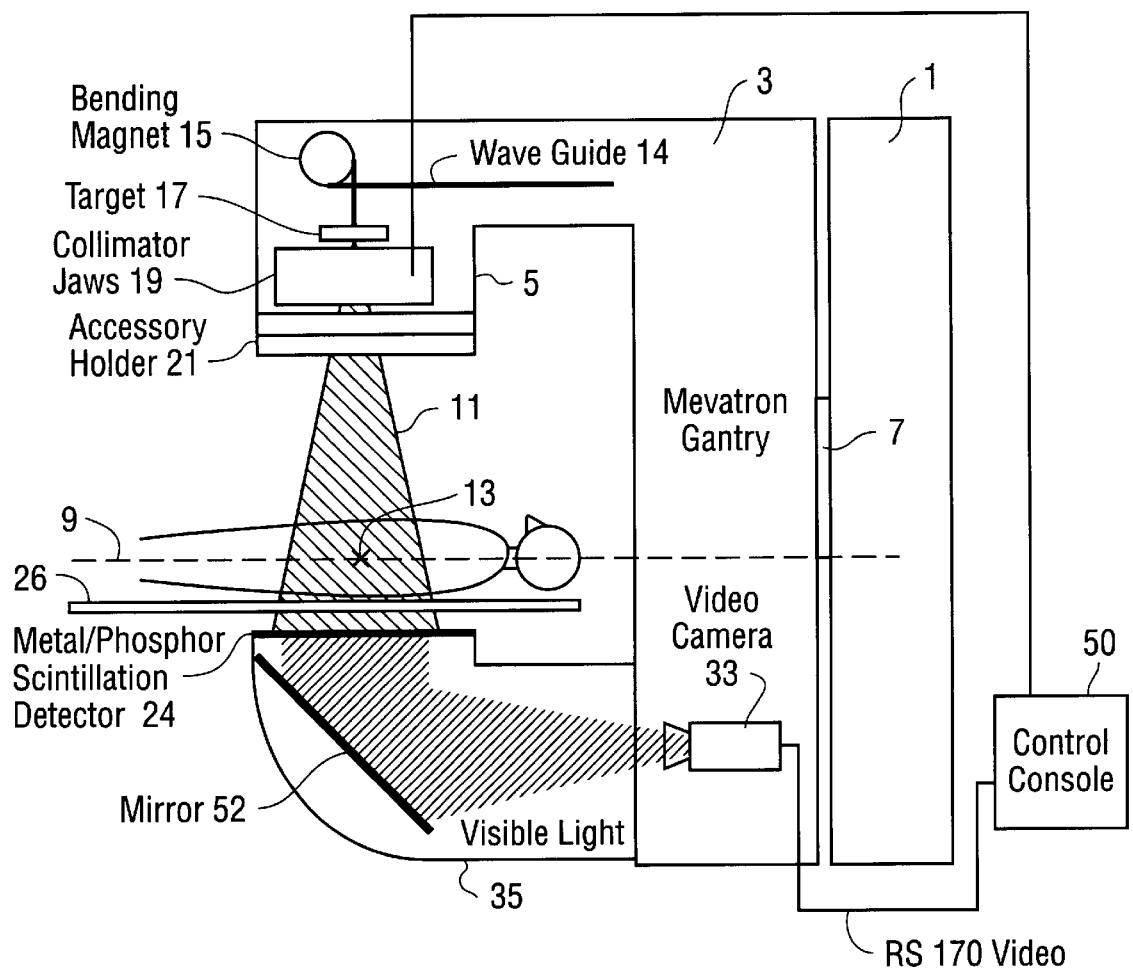
FIG. 1 illustrates a radiation beam treatment apparatus having a retractable imaging device.

One example of a linear accelerator treatment device is described in U.S. Pat. No. 5,138,647 issued Aug. 11, 1992 to Nguyen et al. FIG. 1 is a schematic diagram of a device similar to that described in U.S. Pat. No. 5,138,647. FIG. 1 shows a linear accelerator device with a stand 1 which is typically anchored firmly to the floor. Stand 1 supports a gantry 3 including a treatment head 5. Gantry 3 can be rotated on bearing 7 around a horizontal axis 9. Within gantry 3 and treatment head 5 are shown to include a wave guide 14 which channels energy. Wave guide 14 is shown to be coupled with a bending magnet 15 which directs the energy beam 11 through target 17 and into collimator 19. The resulting 11 beam may also optionally be radiated through some type of accessory in the accessory holder 21.

In stand 1, an electron injector is typically provided which supplies injector pulses to an electron gun arranged in gantry 3. Electrons are emitted from the electron gun into wave guide 14 to be accelerated. An electromagnetic field supplied to wave guide 14 typically accelerates the electrons emitted by the electron gun for forming an electron beam. In treatment head 5, the electron beam typically enters an evacuated envelop which bends the electron beam, for example, by 270 degrees. The electron beam then typically leaves the envelop through a window. If electron radiation is to be generated, a scattering foil is typically moved into the trajectory of the electron beam. If x-ray radiation is to be generated, a target is typically moved into the trajectory. The energy level of the electron beam is caused to be higher than during the generation of the electron radiation because more energy is necessary for generating x-ray radiation due to deceleration of the electrons in the target. The x-rays are typically of penetrating power and may be used for the treatment of deep seated tumors, whereas the electrons themselves may be used directly to treat more superficial cancers. During treatment, the patient rests on a treatment couch 26 and intersects the treatment area at an isocenter 13.

At a front surface of the side of gantry 3, a retractable and collapsible portal imaging detector housing 35 allows radiation treatment to be performed simultaneously with visualization of the patient's anatomy within the x-ray radiation beam. After passing through the patient's body, the x-rays impinge upon image detector 24, is reflected off mirror 52, and captured by a video camera 33. The video camera may be coupled with an integrated treatment work station, such as control console 50, wherein the functions and control of the video camera may be controlled in the same system as the functions and control of gantry 3 adjustments. The control console 50 may be a standard computer configured to process, store, and display images captured by the video camera 33, and also control the gantry 3 adjustments as well as receiving and processing data from other components, such as the collimator 19. One example of a control console 50 that may be used with the present invention is a VME based 486 processor, 50 MHz, using a real time operating system such as RMOS 2. An example of a software that may be run on such a control console 50 is Siemens Control Console version 7.2.

Control console 50 can also receive data identifying the position of the collimator 19. For example, the multi-leaf collimator 19 may send hexadecimal numbers to the control console 50, indicating the collimator leaf positions.

Alternatively, video camera 33 may be coupled with a computer system which may be electronically accessible by another computer system, wherein the second computer system controls the motions and adjustments of gantry 3. Yet another alternative is for video camera 33 to be coupled to a video camera computer system while the motions and control of gantry 3 are coupled to a separate computer system.

Figure 2:
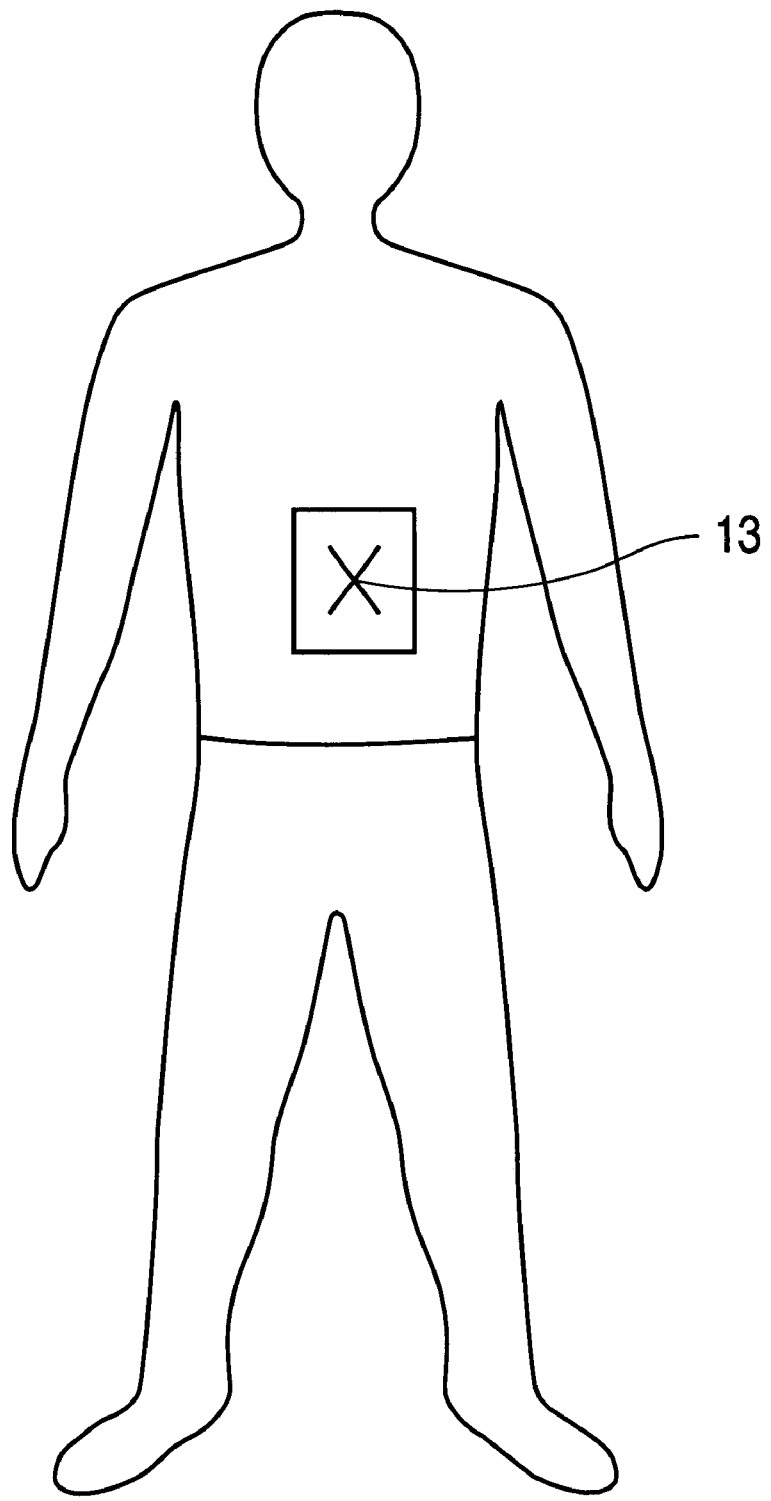
FIG. 2 is an illustration of isocenter.

FIG. 2 is an illustration of isocenter. FIG. 2 illustrates a patient with isocenter 13 located at the three-dimensional center of the treatment field. Isocenter 13 is located in the center of the treatment field from a perspective above the patient, as well as the center of the patient within the treatment field as seen from a perspective beside the patient (see isocenter 13 of FIG. 1). All other points within the treatment field may be defined relative to isocenter 13. For example, patient positioning, treatment field size, and treatment field shape may be defined relative to isocenter 13. A two-dimensional image also has a two-dimensional projection of the isocenter corresponding to the three-dimensional isocenter. Once the two-dimensional projection of the isocenter is determined, then all equipment calibrations, image comparisons and patient positioning may be performed with respect to the projection of the isocenter. If detector housing 35 is centered and gantry 3 is centered above detector housing 35, then the projection of the isocenter should be at the center of the image. However, if detector housing 35 is not exactly centered or if gantry 3 is not centered above detector housing 35, then it is typically unclear where the projection of the isocenter is located.

Figure 3:
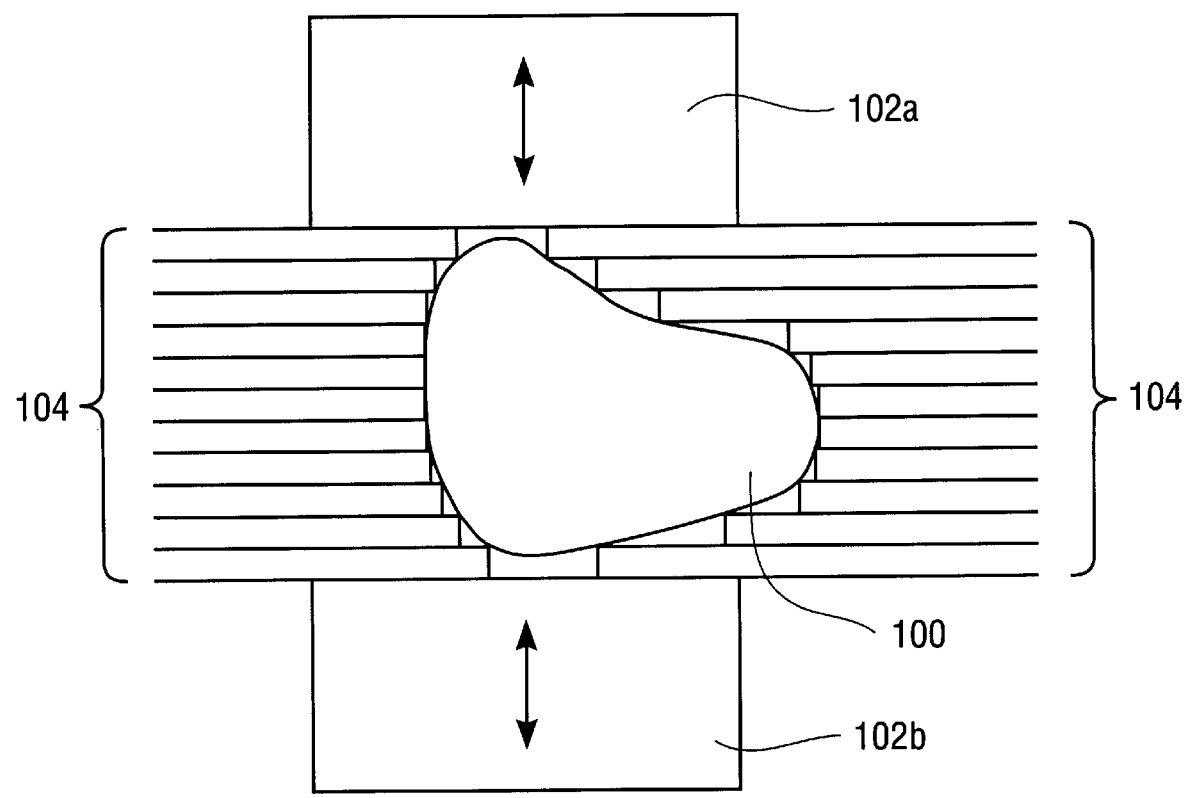
FIG. 3 is an illustration of a multi-leaf collimator.

FIG. 3 is an illustration of a multi-leaf collimator 19. In the example shown in FIG. 3, a multi-leaf collimator 19 is shown to be shaped around a target 100, such as a tumor. Tumor shapes are often irregular, and a multi-leaf collimator, such as the multi-leaf collimator manufactured by Siemens, facilitates minimal radiation being applied to non-tumor tissues by shaping itself close to the shape of the tumor.

Multi-leaf collimator 19 is shown to include leaves 104 located on either side of target 100. Additionally, multi-leaf collimator 19 may also include a set of jaws 102a–102b located perpendicular to leaves 104. Jaws 102a–102b may be movable in a direction perpendicular to the longitudinal axis of leaves 104. Accordingly, jaws 102a–102b may approach each other to reduce the size of the x-ray field, or move away from each other to increase the size of the x-ray field. Likewise, each leaf 104 may be moved along it's longitudinal axis toward or away from an opposing leaf 104 to customize the x-ray field for a particular target 100, such as a tumor. The x-ray field is allowed to pass within the space between leaves 104 and jaws 102a–102b.

When the multi-leaf collimator 19 is shaped substantially similar to target 100, it facilitates a very high dosage to be applied to target 100, while still protecting healthy tissue and vital organs. However, even if multi-leaf collimator 19 is shaped substantially similar to target 100, healthy tissue and vital organs may be damaged if multi-leaf collimator 19 is not matched to the location of target 100.

Figure 4:
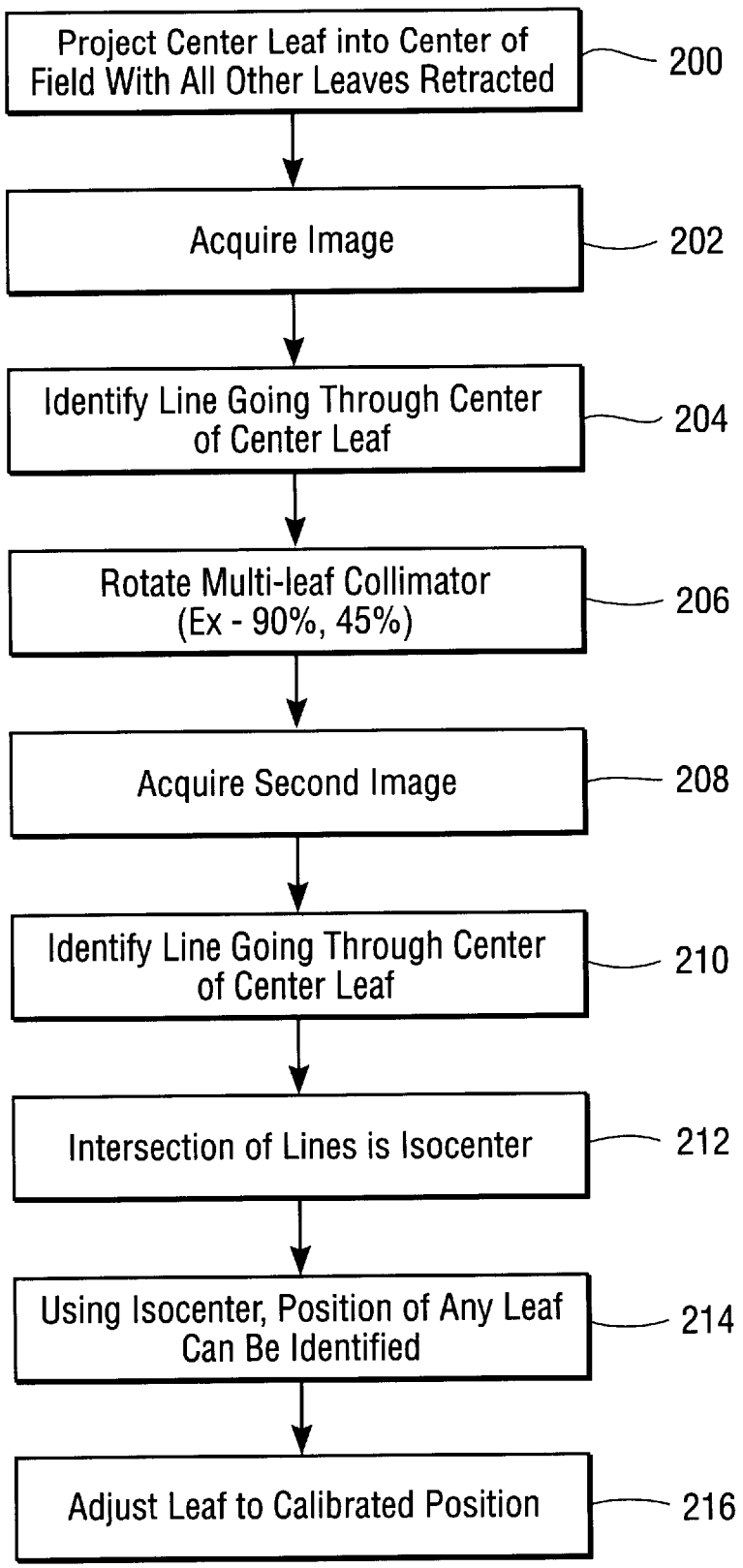
FIG. 4 is a flow diagram according to an embodiment of the present invention for locating a projection of the isocenter by using a multi-leaf collimator.
Figure 5A:
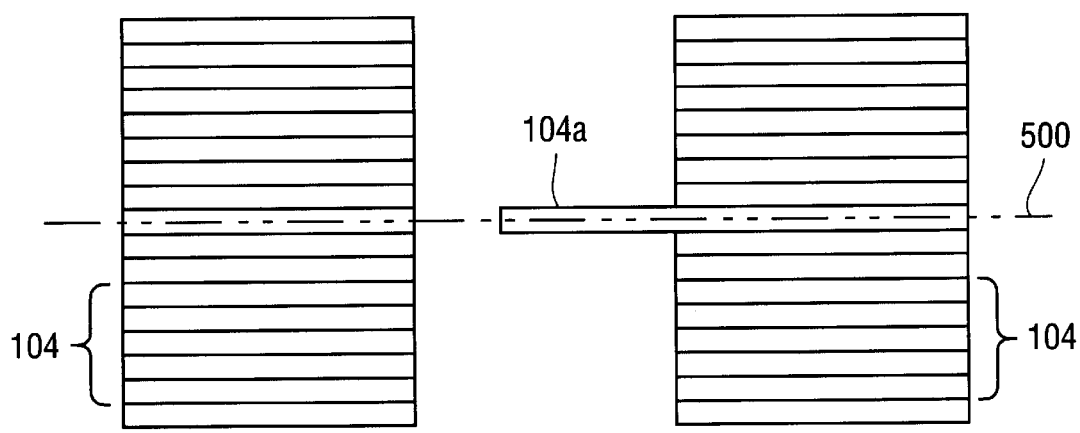
FIGS. 5a–5c depict a multi-leaf collimator in various stages of determining a projection of the isocenter according to an embodiment of the present invention.
Figure 5B:
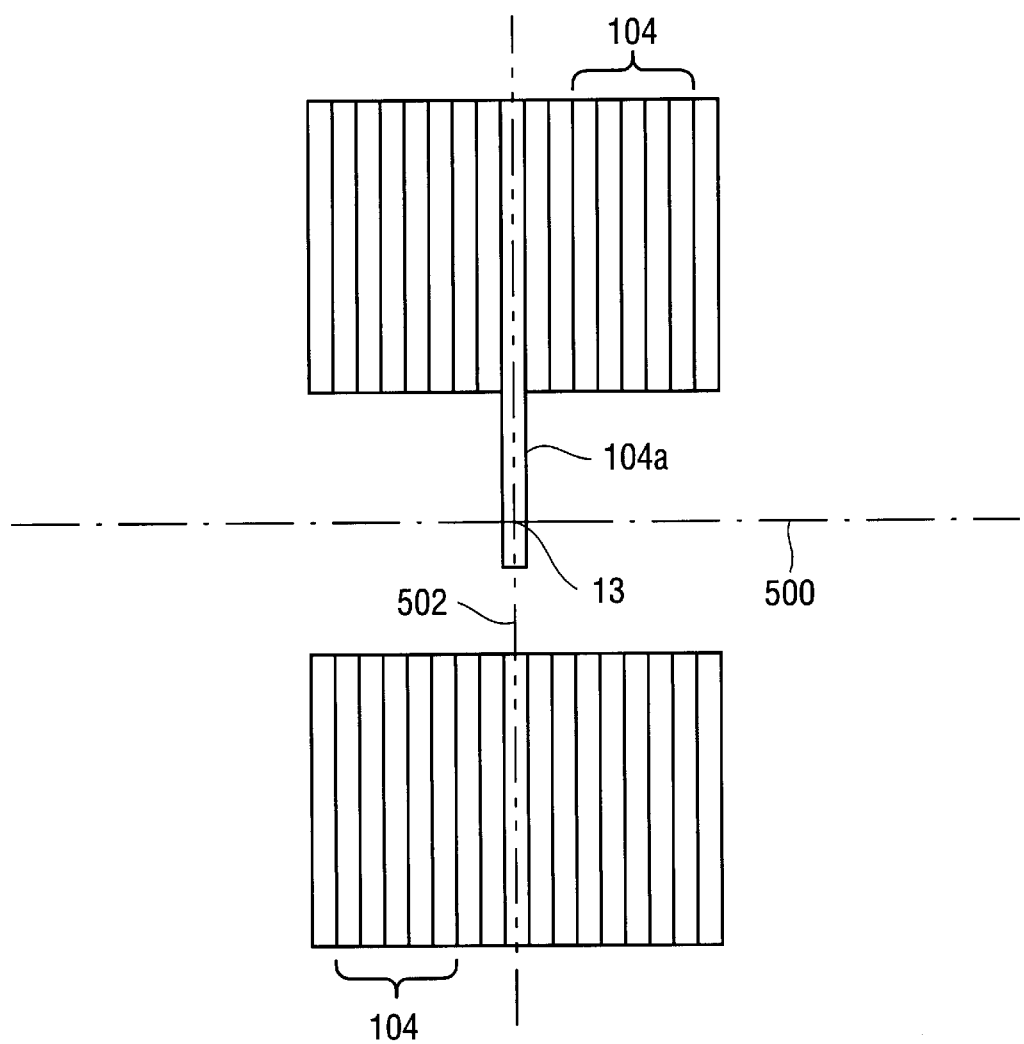
Figure 5C:
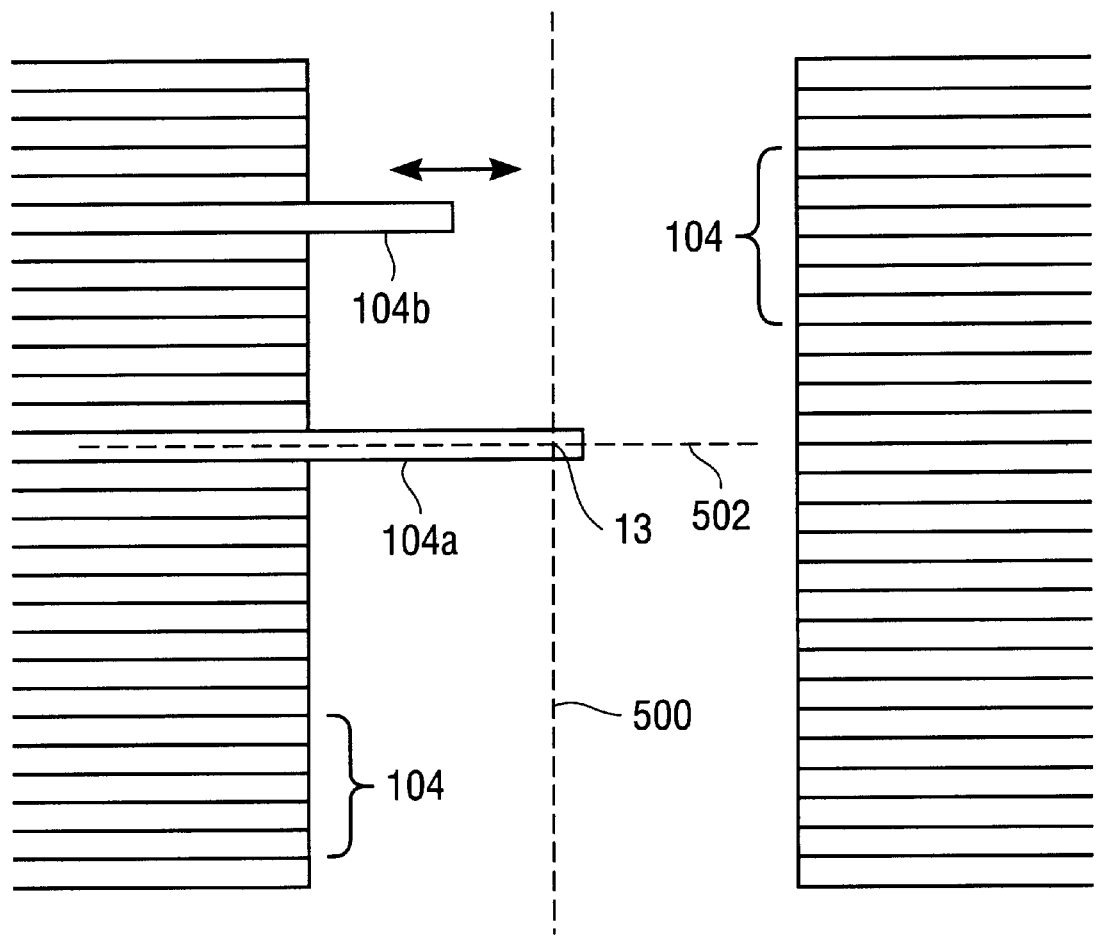

FIG. 4 is a flow diagram of a method according to an embodiment of the present invention for locating the projection of the isocenter by utilizing a multi-leaf collimator. The method shown in FIG. 4 may be referenced in conjunction with FIGS. 5a–5c. FIGS. 5a–5c illustrate a multi-leaf collimator in various positions at various steps described in the method according to an embodiment of the present invention exemplified in FIG. 4.

A center leaf of a multi-leaf collimator is projected into the center of a field with all other leaves retracted (step 200). In FIG. 5a, a center leaf 104a is shown to be projected into the center of a field, such as an x-ray field, with all other leaves 104 retracted. In the example of a Siemens multi-leaf collimator, there may be 29 leaves on each side of the field for a total of 58 leaves plus two jaws (shown in FIG. 3). In this example, a center leaf is leaf 15 (the 15$^{th}$ leaf counted from either direction).

An image is acquired through the multi-leaf collimator (step 202). A line through the longitudinal center of the center leaf is then identified (step 204). In the example shown in FIG. 5a, the line through the longitudinal center of center leaf 104a is line 500. Since isocenter is theoretically in the center of the field, and the shape of the field is defined by the multi-leaf collimator, the center leaf 104a should be located in the middle of the field. Additionally, the width of each leaf is expected to be uniform and all of the leaves are positioned flush against each other so that the width of the collimator perpendicular to the longitudinal axis of the leaves are expected to remain constant. Accordingly, line 500 is a line moving through the projection of the isocenter.

Once line 500 has been identified, the multi-leaf collimator is then rotated (step 206). For example, the multi-leaf collimator may be rotated 90 degrees or 45 degrees. In the is example shown in FIG. 5b, the multi-leaf collimator has been rotated 90 degrees as compared to its position shown in FIG. 5a.

A second image is then acquired by allowing the field to flow through the collimator (step 208). Once the second image has been acquired, a second line moving through the longitudinal center of center leaf 104a is identified (step 210). In the example shown in FIG. 5b, the second line moving through the longitudinal center of center leaf 104a is shown to be line 502.

The intersection of lines 500 and 502 is then identified as the projection of the isocenter (step 212). If the multi-leaf collimator is rotated at a different angle, such as two 45 degree turns, and a third line (not shown) is identified, then the intersection of all three lines would be identified as the projection of the isocenter. If fewer than all lines intersect at one point, then the point at which the majority of the lines intersect would be identified as the projection of the isocenter and the remaining lines may be attributed to mechanical error.

Once the projection of the isocenter is located, the position of any leaf may be identified with respect to the projection of the isocenter 13 (step 214). Accordingly, the position of any leaf in the multi-leaf collimator may be calibrated with respect to the projection of the isocenter 13 (step 216). In the example shown in FIG. 5c, a second leaf 104b is shown to be in a specified position. The position of leaf 104b may be calibrated with respect to the projection of the isocenter 13 to ensure accuracy and precision despite mechanical errors in the positioning of leaf 104b.

Figure 6:
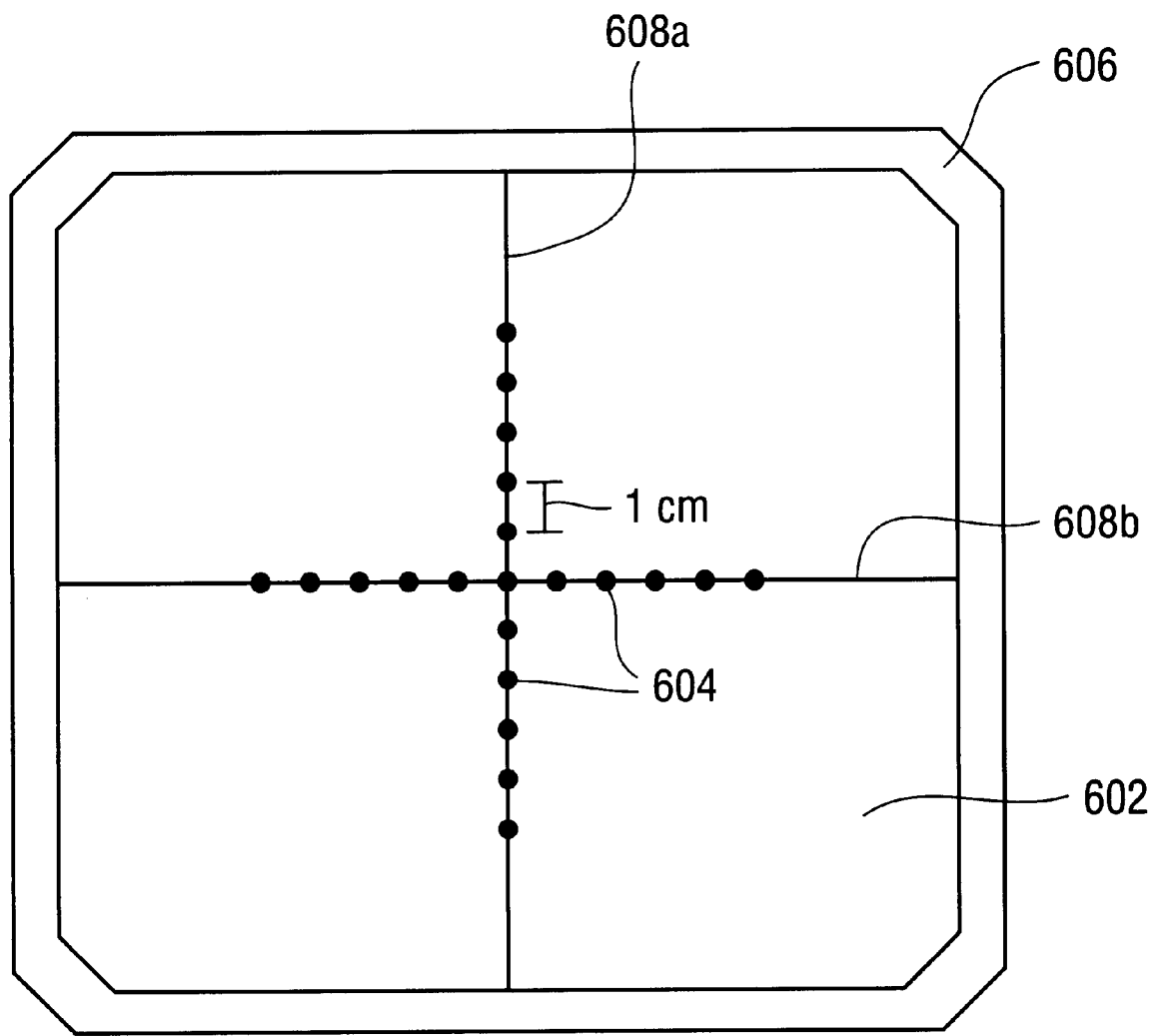
FIG. 6 is an illustration of an accessory according to an embodiment of the present invention which may be used to determine a projection of the isocenter.

FIG. 6 is an illustration of an accessory which may be used to find the projection of the isocenter according to another embodiment of the present invention. Accessory 600 may be a clear piece of plastic 602 surrounded by a frame 606. The frame 606 should be a compatible size with the accessory holder of the radiation treatment apparatus, such as accessory holder 21 of the radiation treatment apparatus of FIG. 1. Examples of the size of accessory 600 include approximately 21 cm×25 cm, or 25 cm×25 cm. Within clear plastic 602, metal markers 604 may be placed. A metal marker should be located in the center of the clear plastic 602, preferably with several other metal markers spaced apart at a predetermined distance such as approximately 5 mm. The metal marker may be a spot of metal embedded or located in the plastic 602. The metal marker is preferably a metal which will stop radiation, such as Tungsten, and large enough to show in an image. An example of a size of a metal marker is approximately 1–2 mm in diameter. Metal markers 604 may be spaced apart on an X and Y axis 608a–608b. A metal marker should be placed at the intersection of the X and Y axis 608a–608b to indicate the projection of the isocenter. The center metal marker placed at the X and Y axis 608a–608b may be a larger marker than some of the other markers. For example, the center metal marker may be 2 mm in diameter, followed by a predetermined number of smaller metal markers, such as four metal markers 1 mm each in diameter, then followed by another 2 mm metal marker, followed again by four more 1 mm metal markers.

The x-ray field is typically at such a high energy that most of the x-ray beam will move through the body of the patient. Accordingly, only hard locations in the patient's body, such as a bone structure, may be viewed in an image taken of the patient. However, if the high energy x-ray field is shot through accessory 600 as well as the patient, then a resulting image should show metal markers 604. The center metal marker is expected to be the projection of the isocenter of the image. If the center metal marker is not visible in the image (for example a bone structure is also located at the projection of the isocenter) then the remaining metal markers 604 may be used to determine the projection of the isocenter since all the metal markers are evenly spaced at a predetermined distance, such as 5 mm.

Figure 7:
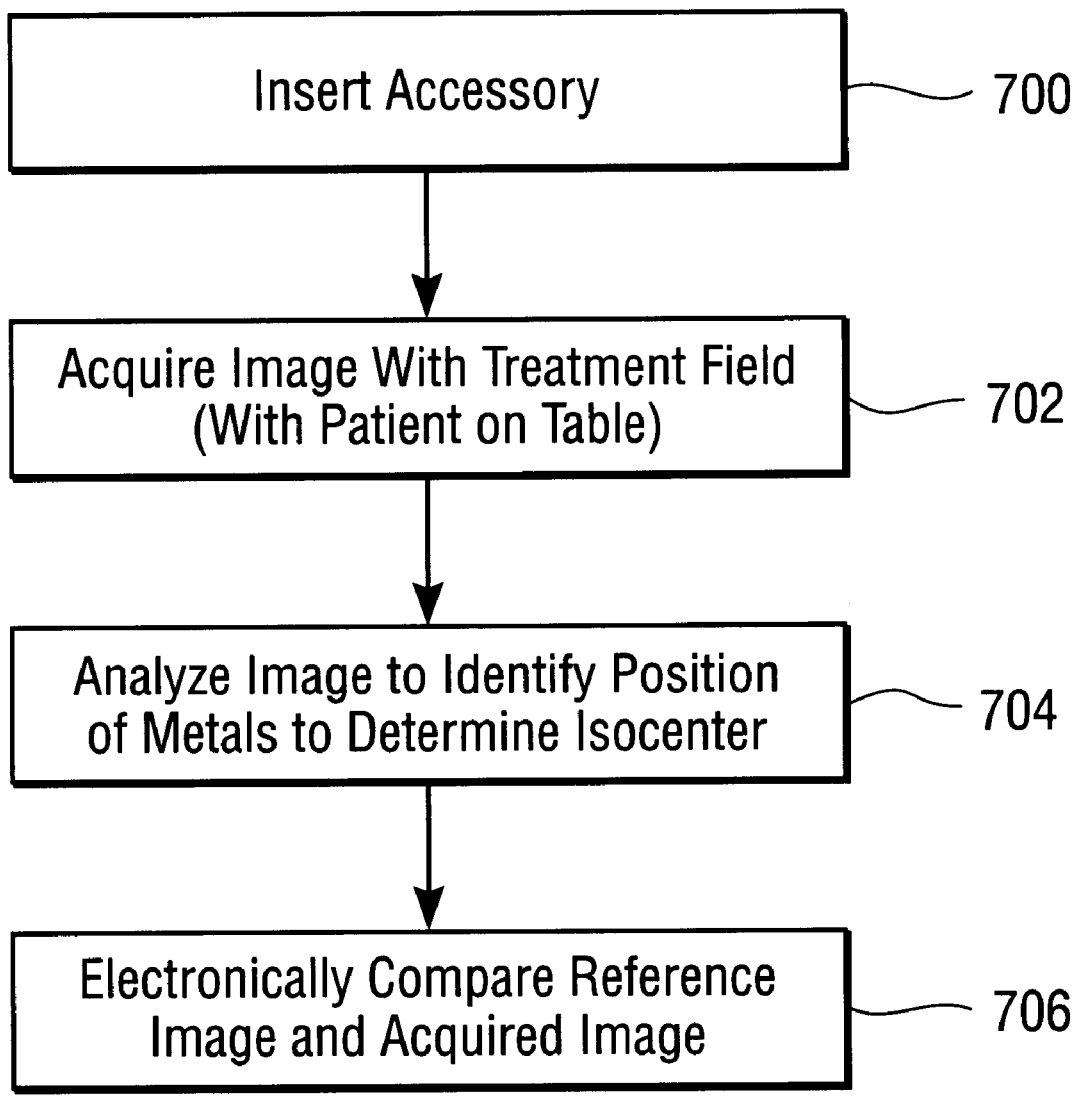
FIG. 7 is a flow diagram of a method according to an embodiment of the present invention for finding a projection of the isocenter by using an accessory.

FIG. 7 is a flow diagram of a method according to an embodiment of the present invention for locating the projection of the isocenter by using an accessory. Accessory 600 is inserted into a radiation treatment apparatus, such as into accessory holder 21 of the apparatus shown in FIG. 1 (step 700). An image is then acquired with the treatment field moving through accessory 600 as well as the patient positioned on the table (step 702). The image is then analyzed to identify the position of metal markers 604 to determine the projection of the isocenter of the image (step 704). Once the projection of the isocenter has been identified, the acquired image may be electronically compared to a reference image (step 706). The electronic comparison may be performed through known algorithms, such as the Basic Pattern Recognition Module included in Matrox Imaging Library (MIL) manufactured by Matrox.

Figure 8:
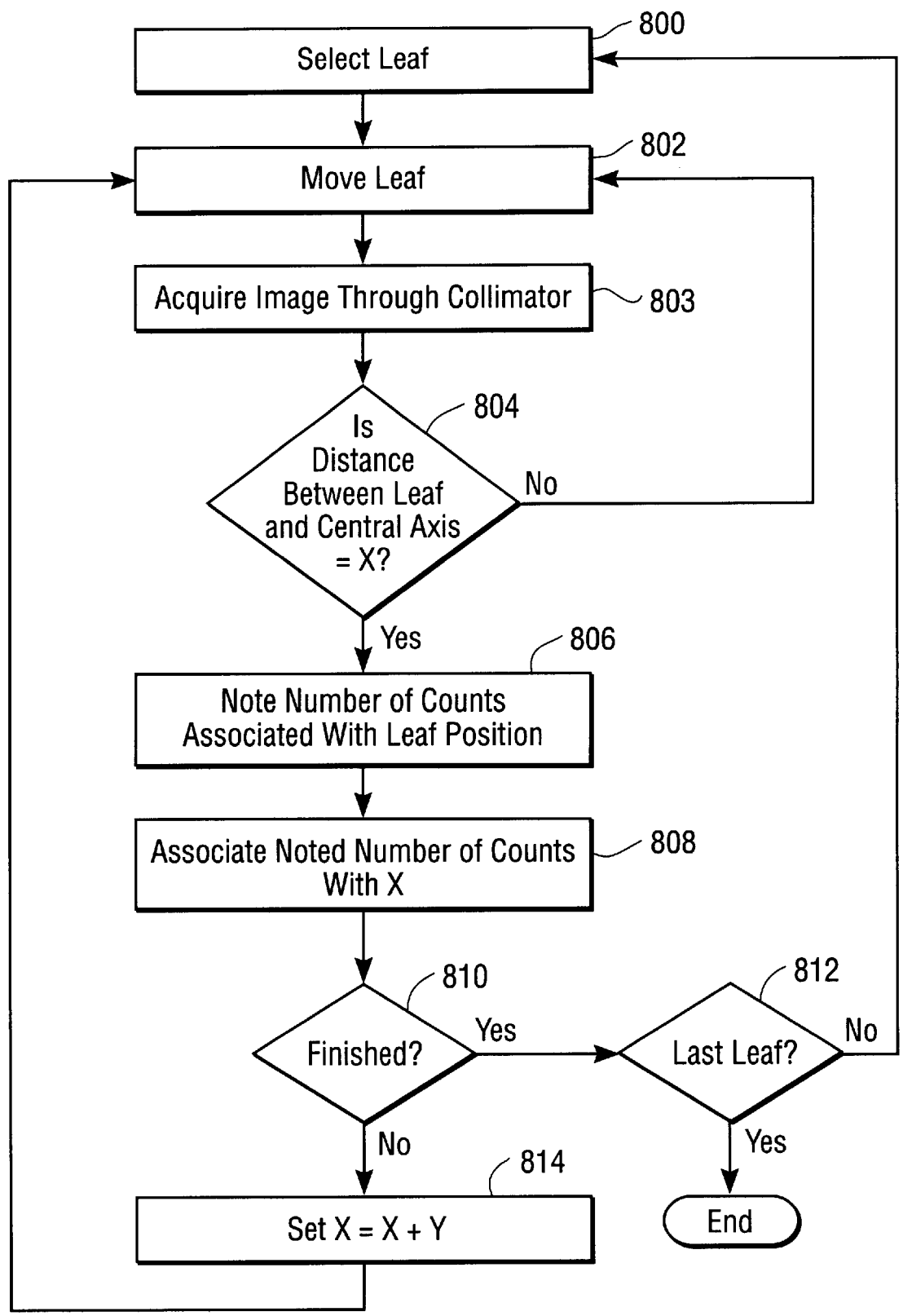
FIG. 8 is a flow diagram of a method according to an embodiment of the present invention for calibrating a collimator.

FIG. 8 is a flow diagram of a method according to an embodiment of the present invention for calibrating a collimator. A leaf of a multi-leaf collimator is selected (step 800). The selected leaf is then moved (step 802). An image is acquired through the collimator (step 803). It is then determined whether the projection of the selected leaf onto the image detector 24 (of FIG. 1) equals a predetermined distance from a central axis (step 804). This step is illustrated in FIG. 9.

Figure 9:
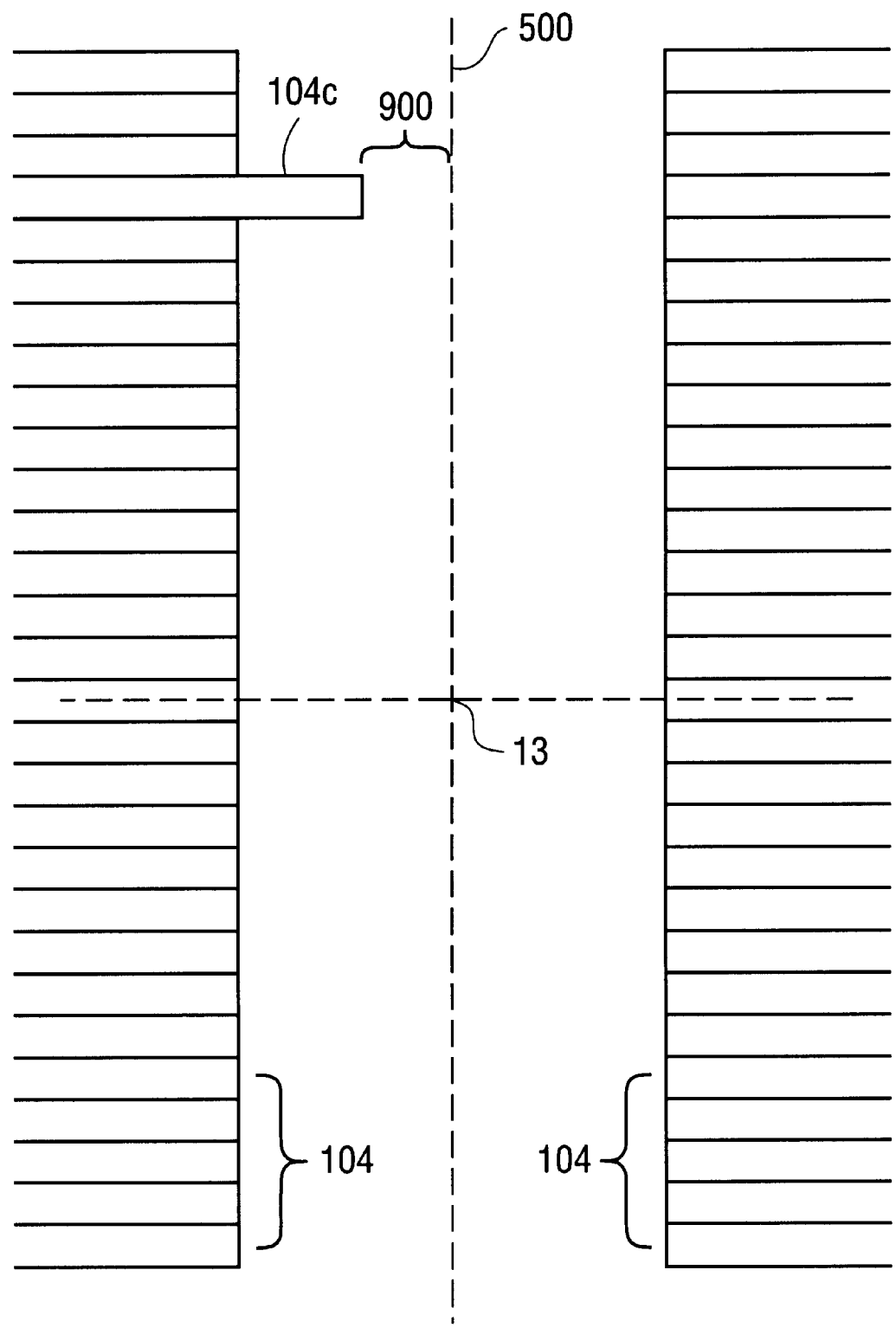
FIG. 9 is an illustration of a multi-leaf collimator during a calibration according to an embodiment of the present invention.

FIG. 9 is an illustration of a multi-leaf collimator during a calibration according to an embodiment of the present invention. FIG. 9 shows an example of the method described in FIG. 8. FIG. 9 shows the leaves 104 of the multi-leaf collimator, as well as the projection of the isocenter 13. A central axis 500 is shown to cross through the projection of the isocenter 13. If the leaf that is selected in step 800 of FIG. 8 is leaf 104C, then leaf 104C is moved. It is then determined whether the distance 900 between the edge of leaf 104C and the central axis 500 is equal to a predetermined distance, such as X mm.

If the distance 900 between the selected leaf 104C and the central axis 500 does not equal X (step 804 of FIG. 8), then the selected leaf 104C is moved again (step 802) until the distance 900 between the selected leaf 104C and the central axis 500 equals X. When the distance 900 equals X, then a number of counts associated with the collimator leaf 104C position is then noted (step 806).

Multi-leaf collimators, such as collimator 19 of FIG. 3, typically use a number, such as a hexadecimal number, to identify leaf positions. This number identifying a leaf position is herein referred to as the number of counts. The collimator typically includes at least one processor measuring these counts. The number of counts associated with a leaf position is regularly sent to the control console, such as control console 50 of FIG. 1.

The noted number of counts is then associated with the distance X (step 808). The distance X is preferably measured in standard measurement increments such as mm or inches. It is then determined whether the calibration for the selected leaf is finished (step 810). One example of determining when a calibration for a selected leaf is finished is to obtain a set number of data points, such as four data points, so that four separate number of counts are associated with four different distances. When the fourth distance is determined, then the calibration for that selected leaf is finished.

If the calibration for the selected leaf is finished, then it is determined whether the selected leaf was the last leaf (step 812). If the selected leaf was the last leaf, then the calibration is completed. If, however, the selected leaf is not the last leaf, then another leaf is then selected (step 800).

If the calibration for the selected leaf is not yet finished (step 810), then X is set to X+Y (step 814). For example, if the first data point sets X as 10 mm, then the next data point may be set at 20 mm. Thereafter, the selected leaf is moved (step 802) until the distance between the selected leaf and the central axis equals the new predetermined distance (steps 804–806).

With these data points a conversion between distance, as in millimeters, and multi-leaf collimator counts, such as hexadecimal counts, can be determined.

Although the present invention has been described in accordance with the embodiment shown, one of ordinary skill in the art will readily recognize that there could be variations to the embodiment and these variations would be within the spirit and scope of the present invention. Accordingly, many modifications may be made by one of ordinary skill in the art without departing from the spirit and scope of the appended claims.

What is claimed is:

1. A method for calibrating a collimator comprising:
   moving a leaf of a collimator;
   determining whether a distance between the leaf and a line approximately equals a predetermined measurement; and
   associating the predetermined measurement with a collimator specific count if the distance between the leaf and the line approximately equals the predetermined measurement.

2. The method of claim 1, wherein the line traverses through a projection of the isocenter.

3. The method of claim 1, further comprising determining whether a second distance between the leaf and the line approximately equals a second predetermined measurement.

4. The method of claim 1, further comprising acquiring an image through the collimator.

5. The method of claim 1, wherein the collimator specific count is a hexadecimal number.

6. A system for calibrating a collimator comprising:
   means for moving a leaf of a collimator;
   means for determining whether a distance between the leaf and a line approximately equals a predetermined measurement; and
   means for associating the predetermined measurement with a collimator specific count if the distance between the leaf and the line approximately equals the predetermined measurement.

7. The system of claim 6, wherein the line traverses through a projection of the isocenter.

8. The system of claim 6, further comprising means for acquiring an image through the collimator.

9. The system of claim 6, wherein the collimator specific count is a hexadecimal number.

10. A system for calibrating a collimator comprising:
a collimator including a leaf;
an image capturing device configured to capture an image of the collimator; and
a processor configured to determine whether a distance between the leaf and a line approximately equals a predetermined measurement.

11. The system of claim 10, wherein the processor is also configured to associate the predetermined measurement with a collimator specific count if the distance between the leaf and the line approximately equals the predetermined measurement.

12. The system of claim 10, wherein the line traverses through a projection of the isocenter.

13. The system of claim 10, wherein the collimator specific count is a hexadecimal number.

* * * * *